United States Patent
Bathe et al.

(10) Patent No.: US 6,531,503 B1
(45) Date of Patent: Mar. 11, 2003

(54) BENZOFURANE DERIVATIVES

(75) Inventors: Andreas Bathe, Darmstadt (DE); Bernd Helfert, Obert-Ramstadt (DE); Henning Böttcher, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/030,471

(22) PCT Filed: Jun. 29, 2000

(86) PCT No.: PCT/EP00/06089

§ 371 (c)(1),
(2), (4) Date: Jan. 9, 2002

(87) PCT Pub. No.: WO01/04112

PCT Pub. Date: Jan. 18, 2001

(30) Foreign Application Priority Data

Jul. 10, 1999 (DE) .......................... 199 32 314

(51) Int. Cl.⁷ .................. A61K 31/40; A61K 31/34
(52) U.S. Cl. .............. 514/422; 514/252.13; 514/254.1; 514/469; 549/469; 548/525; 544/357; 544/359
(58) Field of Search .................. 549/469; 548/525; 544/357, 359; 514/252.13, 254.1, 422, 469

(56) References Cited

FOREIGN PATENT DOCUMENTS

| EP | 0648767 | 4/1995 |
|----|---------|--------|
| EP | 0738722 | 10/1996 |
| WO | 79 00426 | 7/1979 |
| WO | 94 29290 | 12/1994 |

OTHER PUBLICATIONS

Dauzonne D et al.: "Synthesis and some CNS activities of new benzofuranylacryloylpiperazines" European Journal of Medicinal Chemistry, Chimica Therapeutica, Fr, Editions Scientifique Elsevier, Paris, vol. 30, No. 1, 1995, pp. 53–59, XP004040119 ISSN: 0223–5234, p. 53, col. 2; example 5 abstract.

*Primary Examiner*—Amelia Owens
(74) *Attorney, Agent, or Firm*—Millen, White, Zelano & Branigan, P.C.

(57) ABSTRACT

Benzofurane derivatives of formula (I), wherein R and R' have the meanings given in claim no. (1), and salts thereof are suitable for use as intermediate products in the synthesis of medicaments.

16 Claims, No Drawings

BENZOFURANE DERIVATIVES

The invention relates to benzofuran derivatives of the formula I.

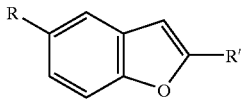

in which
- R is 1-piperazinyl, 4-$R^1$-piperazinyl or L,
- R' is 2-$R^2$-5-$R^3$-pyrrol-1-ylcarbonyl, 4-$R^4$-piperazinyl-1-ylcarbonyl, N,N-di(tert-butyloxy-carbonyl) aminocarbonyl, —CH=C($R^5R^6$), benzofuran-2-yl-C≡C—, —C(Hal)$_3$, —CO—C(Hal)$_3$, 1,4-dihydrobenzo[d][1,2]oxazin-3-ylcarbonyl or 3,4-dihydrobenzo-1H-phthalazin-2-ylcarbonyl,
- L is Cl, Br, I or a free or reactive functionally modified OH group,
- $R^1$, $R^4$ in each case independently of one another are H, benzyl or another amino protective group,
- $R^2$, $R^3$ in each independently of one another are H or alkyl having 1–6 C atoms,
- $R^5$, $R^6$ in each case independently of one another are alkyl having 1–6 C atoms,
- Hal is F, Cl, Br or I, and their salts.

Similar compounds are disclosed in DE 43 33 254 and DE 195 14 567.

The invention was based on the object of finding novel compounds which can be used, in particular, as intermediates in the synthesis of medicaments, but can also be used directly for the production of medicaments.

It has been found that the compounds of the formula I and their salts are important intermediates for the production of medicaments and at the same time have pharmacological properties. Thus, they show, for example, effects on the central nervous system.

The invention relates to the benzofuran derivatives of the formula I and their salts.

Above and below, the radicals $R^1$, $R^2$, $R^3$, $R^4$, $R^5$, $R^6$, R, R', L, Q and Q' have the meanings indicated in the formulae I to V, if not expressly stated otherwise. In the above formulae, A has 1 to 4, preferably 1, 2 or 3, C atoms. A is preferably methyl or ethyl, furthermore propyl or isopropyl, and additionally also butyl, isobutyl, sec-butyl or tert-butyl. The radical Ph is phenyl.

In the compounds of the formula [sic] I, II, V, VI and VII, L, Q and Q' are preferably Cl, Br, I or a reactive modified OH group such as, for example, an activated ester, an imidazolide or alkylsulfonyloxy having 1–6 C atoms (preferably methylsulfonyloxy) or arylsulfonyloxy having 6–10 C atoms (preferably phenyl- or p-tolylsulfonyloxy).

The expression "amino protective group" is generally known and relates to groups which are suitable for protecting (for blocking) an amino group from chemical reactions, but which are easily removable after the desired chemical reaction has been carried out at other positions in the molecule. Typical of such groups are, in particular, unsubstituted acyl, aryl, aralkoxymethyl or aralkyl groups. As the amino protective groups are removed after the desired reaction (or reaction sequence), their nature and size is otherwise uncritical; preferred groups, however, are those having 1–20, in particular 1–8 C atoms. The expression "acyl group" is to be interpreted in the widest sense in connection with the present process and the present compounds. It includes acyl groups derived from aliphatic, araliphatic, aromatic or heterocyclic carboxylic acids or sulfonic acids and also, in particular, alkoxycarbonyl, aryloxycarbonyl and especially aralkoxycarbonyl groups. Examples of acyl groups of this type are alkanoyl such as acetyl, propionyl, butyryl; aralkanoyl such as phenylacetyl; aroyl such as benzoyl or toluyl; aryloxyalkanoyl such as phenoxyacetyl; alkoxycarbonyl such as methoxycarbonyl, ethoxycarbonyl, 2,2,2-trichloroethoxycarbonyl, BOC (tert-butoxycarbonyl), 2-iodoethoxycarbonyl; aralkyloxycarbonyl such as CBZ (carbobenzoxycarbonyl, also called "Z"), 4-methoxybenzyloxycarbonyl, FMOC (9-fluorenylmethoxycarbonyl); arylsulfonyl such as Mtr (4-methoxy-2,3,6-trimethylphenylsulfonyl). Preferred amino protective groups are BOC and Mtr, and additionally CBZ or FMOC.

The compounds of the formula I can have one or more chiral centres and therefore occur in various stereoisomeric forms. The formula I includes all these forms.

The invention further relates to a process for the preparation of benzofuran derivatives of the formula I according to claim 1 and of their salts, characterized in that a) for the preparation of compounds of the formula I in which
- R is Cl, Br, I, 1-piperazinyl or 4-$R^1$-piperazinyl and
- R' is 2-$R^2$-5-$R^3$-pyrrol-1-ylcarbonyl, 4-$R^4$-piperazin-1-yl carbonyl, 1,4-dihydrobenzo[d][1,2]-oxazin-3-ylcarbonyl or 3,4-dihydrobenzo-1H-phthalazin-2-ylcarbonyl, a compound of the formula II

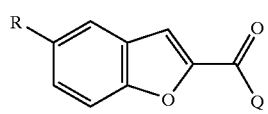

in which
- R is Cl, Br, I, 1-piperazinyl or 4-$R^1$-piperazinyl and
- Q is Cl, Br, I or a free or reactive functionally modified OH group,
- and $R^1$ has the meaning indicated in claim 1 is reacted with a compound of the formula III

R'—H    III in which
- R' is 2-$R^2$-5-$R^3$-pyrrol-1-yl, 4-$R^4$-piperazin-1-yl, 1,4-dihydrobenzo[d][1,2]oxazin-3-yl or 3,4-dihydrobenzo-1H-phthalazin-2-yl,
- and $R^2$, $R^3$ and $R^4$ have the meanings indicated in claim 1, or b) for the preparation of compounds of the formula I in which
- R is Cl, Br, I, 1-piperazinyl or 4-$R^1$-piperazinyl and
- R' is —CH=C($R^5R^6$), benzofuran-2-yl-C≡C—, —C(Hal)$_3$ or —CO—C(Hal)$_3$,
- and $R^1$, $R^5$ and $R^6$ have the meanings indicated in claim 1, i) a compound of the formula IV

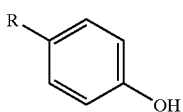

in which
R is Cl, Br, I, 1-piperazinyl or 4-$R^1$-piperazinyl, is reacted with a compound of the formula V

Q'—$CH_2$—CO—R'   V in which R' is —CH=C($R^5R^6$), benzofuran-2-yl-C-≡C—, —C(Hal)$_3$ or —CO—C(Hal)$_3$, and Q' is Cl, Br, I or a free or reactive functionally modified OH group,
and $R^5$ and $R^6$ have the meanings indicated in claim 1, or ii) a compound of the formula Va

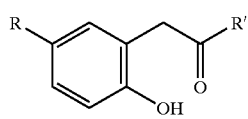

in which R and R' have the meanings indicated under i) is cyclized, or c) a compound of the formula I,
in which R is a 1-piperazinyl radical, is converted by introduction of an amino protective group into another compound of the formula I in which R is the 4-$R^1$-piperazinyl radical,
in which $R^1$ is an amino protective group, or d) a compound of the formula I,
in which R is a 4-$R^1$-piperazinyl group, in which $R^1$ is benzyl or another amino protective group, is converted by removal of the benzyl or amino protective group into a compound of the formula I in which $R^1$ is 1-piperazinyl, or e) in a compound of the formula I a radical R is converted into another radical R
by, for example,
   i) replacing a Br atom by OH,
   ii) esterifying an OH group or
   iii) replacing a Br atom by a 4-$R^1$-piperazinyl group, in which $R^1$ is benzyl or an amino protective group,
and/or a base of the formula I is converted into one of its salts by treatment with an acid.

The compounds of the formula I' and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart), namely under reaction conditions which are known and suitable for the reactions mentioned. In this case, use can also be made of variants which are known per se but not mentioned here in greater detail.

If desired, the starting substances can also be formed in situ such that they are not isolated from the reaction mixture, but immediately reacted further to give the compounds of the formula I.

In the compounds of the formula II, the radical Q is preferably Cl or Br; however, it can also be I, OH or a reactive modified OH group such as alkylsulfonyloxy having 1–6 C atoms (preferably methylsulfonyloxy) or arylsulfonyloxy having 6–10 C atoms (preferably phenyl- or p-tolylsulfonyloxy, 1- or 2-naphthalenesulfonyloxy). In the compounds of the formula II, the radical R is preferably Br or 4-benzylpiperazinyl. The compounds of the formula II are known in some cases; the unknown compounds can easily be prepared analogously to the known compounds.

The reaction of the compounds of the formula II with compounds of the formula III proceeds according to methods such as are known from the literature for the alkylation of amines. The components can be fused with one another without a solvent being present, if appropriate in a closed tube or in an autoclave. However, it is also possible to react the compounds in the presence of an inert solvent. Suitable inert solvents are, for example, hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; amides such as acetamide, dimethylacetamide or dimethylformamide (DMF); nitriles such as acetonitrile; sulfoxides such as dimethyl sulfoxide (DMSO); carbon disulfide; nitro compounds such as nitromethane or nitrobenzene; esters such as ethyl acetate, and optionally also mixtures of the solvents mentioned with one another or mixtures with water.

The addition of an acid-binding agent, for example of an alkali metal or alkaline earth metal hydroxide, carbonate or bicarbonate or of another salt of a weak acid of the alkali metals or alkaline earth metals, preferably of potassium, sodium or calcium, or the addition of an organic base such as triethylamine, dimethylamine, pyridine or quinoline or of an excess of the amine component can be favourable. Depending on the conditions used, the reaction time can be between a few minutes and 14 days, and the reaction temperature between 0 and 150°, normally between 20 and 130° C.

In the compounds of the formula V, the radical Q' is preferably Cl or Br; however, it can also be I, OH or a reactive modified OH group such as alkylsulfonyloxy having 1–6 C atoms (preferably methylsulfonyloxy) or arylsulfonyloxy having 6–10 C atoms (preferably phenyl- or p-tolylsulfonyloxy, or 1- or 2-naphthalenesulphonyloxy).

In the compounds of the formula IV, the radical R is preferably Br or 4-benzylpiperazinyl.

The reaction of the compounds of the formula IV with compounds of the formula V proceeds according to methods such as are known from the literature for the alkylation of phenols.

The compounds of the formula VI are known in some cases; the unknown compounds can easily be prepared analogously to the known compounds. The cyclization is carried out according to generally known methods.

The removal of an amino protective group from a compound of the formula I—depending on the protective group used—is carried out, for example, using strong acids, expediently using TFA (trifluoracetic acid) or perchloric acid, but also using other strong inorganic acids such as hydrochloric acid or sulfuric acid, strong organic carboxylic acids such as trichloroacetic acid or sulfonic acids such as benzene- or p-toluenesulfonic acid. The presence of an additional inert solvent is possible, but not always necessary.

Suitable inert solvents are preferably organic solvents, for example carboxylic acids such as acetic acid, ethers such as tetrahydrofuran or dioxane, amides such as dimethylformamide, halogenated hydrocarbons such as dichloromethane, in addition also alcohols such as methanol, ethanol or isopropanol, and water. In addition, mixtures of the abovementioned solvents are possible. TFA is preferably used in an excess without addition of a further solvent, perchloric acid in the form of a mixture of acetic acid and 70% perchloric acid, in the ratio 9:1. The reaction, temperatures are expediently between approximately 0 and approximately 50°; the reaction is preferably carried out between 15 and 30°.

The group BOC is preferably removed using TFA in dichloromethane or using approximately 3 to 5 N hydrochloric acid in dioxane at 15–30°.

Hydrogenolytically removable protective groups (e.g. CBZ or benzyl) can be removed, for example, by treating with hydrogen in the presence of a catalyst (e.g. of a noble metal catalyst such as palladium, expediently on a support such as carbon). Suitable solvents here are those indicated above, in particular, for example, alcohols such as methanol or ethanol or amides such as DMF. The hydrogenolysis is generally carried out at temperatures between approximately 0 and 100° and pressures between approximately 1 and 200 bar, preferably at 20–30° and 1–10 bar.

Compounds of the formula I in which R' is N,N-di(tert-butyloxycarbonyl)aminocarbonyl are preferably obtained by reaction of the unprotected aminocarbonyl compound, in which R is 4-$R^1$-piperazinyl or L, L [lacuna] the meaning indicated in claim 1 and $R^1$ is benzyl or another amino protective group, with $(BOC)_2O$ in an inert solvent, such as, for example, THF or dioxane with addition of a base, such as, for example, diethylamine and preferably of a catalytic amount of dimethylaminopyridine.

A base of the formula I can be converted into the associated acid addition salt using an acid, for example by reaction of equivalent amounts of the base and of the acid in an inert solvent such as ethanol and subsequent evaporation. Suitable acids for this reaction are in particular those which give physiologically acceptable salts. Thus, inorganic acids can be used, e.g. sulfuric acid, nitric acid, hydrohalic acids such as hydrochloric acid or hydrobromic acid, phosphoric acids such as ortho-phosphoric acid, sulfamic acid, furthermore organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxy-ethanesulfonic acid, benzenesulfonic acid, p-toluene-sulfonic acid, naphthalenemono- and -disulfonic acids, and laurylsulfuric acid. Salts with physiologically unacceptable acids, e.g. picrates, can be used for the isolation and/or purification of the compounds of the formula I.

On the other hand, compounds of the formula I can be converted using bases (e.g. sodium or potassium hydroxide or carbonate) into the corresponding metal, in particular alkali metal or alkaline earth metal salts, or into the corresponding ammonium salts.

The invention furthermore relates to the use of the compounds of the formula I as intermediates for the synthesis of medicaments. Corresponding medicaments are described, for example, in DE 4333254.

The invention relates in particular to the use of the compounds of the formula I as intermediates for the synthesis of medicaments which exhibit actions on the central nervous system. 1-[4-(5-Cyanoindol-3-yl)butyl]-4-(2-carbamoylbenzofuran-5-yl)piperazine and its salts are very particularly preferably to be mentioned here.

The invention accordingly relates in particular to the use of the compounds of the formula I according to claim 1 in which R is Cl, Br, I or 4-$R^1$-piperazinyl, R' is 2-$R^2$-5-$R^3$-pyrrol-1-ylcarbonyl, 4-$R^4$-piperazin-1-yl carbonyl, 1,4-dihydrobenzo[d][1,2]oxazin-3-ylcarbonyl or 3,4-dihydrobenzo-1H-phthalazin-2-ylcarbonyl, $R^1$ is benzyl or another amino protective group, $R^4$ is H, benzyl or another amino protective group, $R^2$, $R^3$ in each case independently of one another are H or alkyl having 1–6 C atoms, in the synthesis of 1-[4-(5-cyanoindol-3-yl)butyl]-4-(2-carbamoylbenzofuran-5-yl)piperazine and its salts, characterized in that 3-R-6-hydroxybenzaldehyde, in which R is Cl, Br or I, is reacted with a compound of the formula VI

$$X-CH_2-CO-Q \qquad VI$$

in which X is Cl, Br, I or a free or functionally modified OH group,

Q is OH or OR" and

R" is alkyl having 1–6 C atoms, to give a compound of the formula VII

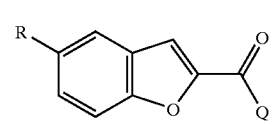

VII in which

R is Cl, Br or I, and Q has the meanings indicated, in that, in the compound thus obtained, Q is converted into Cl, Br, I or a functionally modified OH group, in that the compound thus obtained is reacted with a compound of the formula III

$$R'-H \qquad III$$

in which

R' is 2-$R^2$-5-$R^3$-pyrrol-1-ylcarbonyl, 4-$R^4$-piperazin-1-ylcarbonyl, 1,4-dihydrobenzo[d][1,2]oxazin-3-ylcarbonyl or 3,4-dihydrobenzo-1H-phthalazin-2-ylcarbonyl, and $R^2$, $R_3$ and $R^4$ have the meanings indicated, to give a compound of the formula I in which R is Cl, Br or I, R' is 2-$R^2$-5-$R^3$-pyrrol-1-ylcarbonyl, 4-$R^4$-piperazin-1-ylcarbonyl, 1,4-dihydrobenzo[d][1,2]oxazin-3-ylcarbonyl or 3,4-dihydrobenzo-1H-phthalazin-2-ylcarbonyl, $R^4$ is H, benzyl or another amino protective group, $R^2$, $R^3$ in each case independently of one another are H or alkyl having 1–6 C atoms, in that, in the compound of the formula I thus obtained, the radical R is converted into another radical R, by reacting under transition metal catalysis with a compound of the formula VIII 4-R$^1$-piperazine      VIII in which
R$^1$ is benzyl or another amino protective group,
to give a compound of the formula I
in which
R is 4-R$^1$-piperazinyl,
R' is 2-R$^2$-5-R$^3$-pyrrol-1-ylcarbonyl, 4-R$^4$-piperazin-1-ylcarbonyl, 1,4-dihydrobenzo[d][1,2]oxazin-3-ylcarbonyl or 3,4-dihydrobenzo-1H-phthalazin-2-ylcarbonyl,
R$^1$ is benzyl or another amino protective group,
R$^4$ is H, benzyl or another amino protective group,
R$^2$, R$^3$ in each case independently of one another are H or alkyl having 1–6 C atoms,
in that the compound thus obtained of the formula I
i) is first converted by basic hydrolysis into a compound of the formula IX and/or its acid addition salt

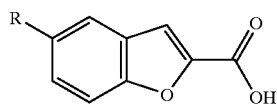
     IX in which
R is 4-R$^1$-piperazinyl and
R$^1$ is benzyl or another amino protective group,
and then converted using ammonia into a compound of the formula X

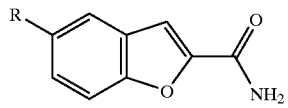
     X in which
R is 4-R$^1$-piperazinyl and
R$^1$ is benzyl or another amino protective group, or
ii) converted directly using ammonia into a compound of the formula X

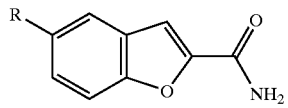
     X in which
R is 4-R$^1$-piperazinyl and
R$^1$ is benzyl or another amino protective group,
in that the compound of the formula X thus obtained is converted into 5-(1-piperazinyl)benzofuran-2-carboxamide or an acid addition salt by removal of the amino protective group R$^1$, and
in that 5-(1-piperazinyl)benzofuran-2-carboxamide is reacted with 3-(4-chlorobutyl)-5-cyanoindole to give 1-[4-(5-cyanoindol-3-yl)butyl]-4-(2-carbamoylbenzofuran-5-yl)piperazine and optionally converted into its acid addition salt.

3-(4-Chlorobutyl)-5-cyanoindole is disclosed in DE 4101686; 1-[4-(5-cyanoindol-3-yl)butyl]-4-(2-carbamoylbenzofuran-5-yl)piperazine is disclosed in DE 4333254.

Above and below, all temperatures are indicated in ° C. In the following examples "customary working up" means: water is added, if necessary, the solution is adjusted, if necessary, to a pH between 2 and 10 depending on the constitution of the final product, and extracted with ethyl acetate or dichloromethane, the organic phase is separated off, dried over sodium sulfate, evaporated and purified by chromatography on silica gel and/or by crystallization. R$_f$ values on silica gel.

EXAMPLE 1

(2,5-Dimethylpyrrol-1-yl)-5-bromobenzofuran-2-yl-methanone

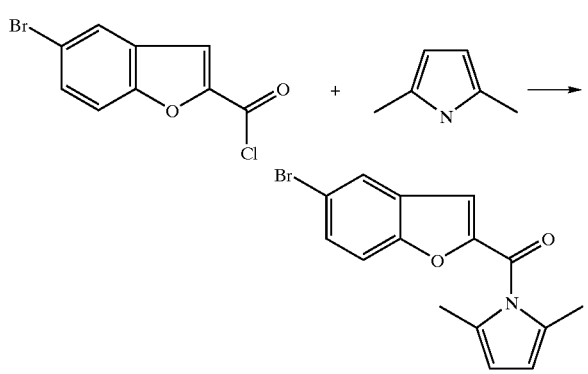

0.3 g of sodium hydride (60% suspension in paraffin oil) is introduced into 10 ml of THF and 0.5 mL [sic] of 2,5-dimethylpyrrole in 10 ml of THF is added dropwise (5 minutes). After stirring at 50° C. for 1 hour, a reddish suspension is present. 1.3 g of 5-bromobenzofuran-2-carbonyl chloride in 10 ml of THF is [sic] added dropwise at 25° C. (5 minutes) and the mixture is subsequently stirred for 2 hours. The addition of 100 ml of completely deionized water and 100 ml of ethyl acetate follows. The separated organic phase was additionally washed 2× with 100 ml of water and concentrated in vacuo. After chromatography on silica gel (eluent heptane/ethyl acetate 4:1), the residual oil gives 700 mg of yellow crystals (yield 44%), m.p. 115–116°.

EXAMPLE 2

5-Bromobenzofuran-2-carboxylic Acid Diethylamide

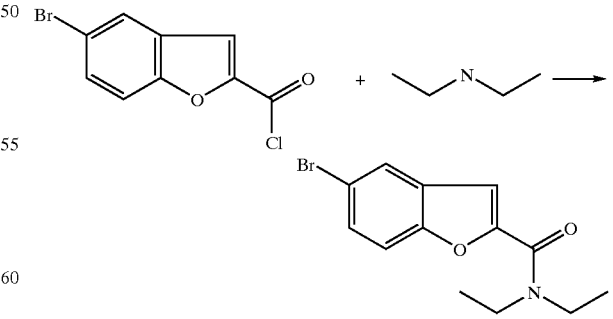

1.3 g. of 5-bromobenzofuran-2-carbonyl chloride, 1 mL [sic] of ethyldiisopropylamine and 30 mL [sic] of toluene are mixed and 0.62 ml of diethylamine is added to the brown-coloured solution with stirring. A precipitate is formed with a slightly exothermic reaction. After 5 minutes, the mixture was treated with 30 ml of completely deionized water and the phases were separated. The organic phase was washed with 1.) 20 ml of iN HCl 2.) 20 ml of iN NaOH 3.) 20 ml of water and then with 20 ml of saturated NaCl solution and then freed of solvent components in vacuo. After chromatography on silica gel the residual, yellowish oil forms in the eluent MtB ether/heptane 2:1 [sic]. Final weight: 1.3 g of colourless crystals [sic] (yield: 88%), m.p. 79–81°.

EXAMPLE 3

Di-tert-Butyl N-(5-Bromobenzofuran-2-carbonyl) imidodicarbonate

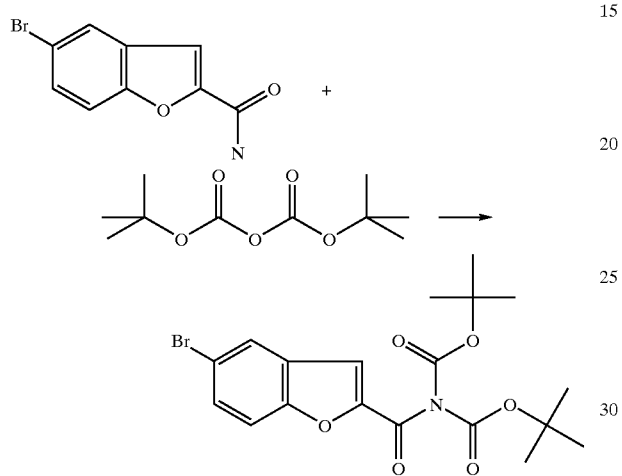

12 g of 5-bromobenzofuran-2-carboxamide, 23.5 ml of BOC$_2$O, 600 mg of DMAP and 8 ml of triethylamine are introduced into 100 ml of THF at 20° C. A clear, orange solution is formed in 3 h in an endothermic reaction. It is warmed to 25° C. and treated with 100 ml of water and 100 ml of ethyl acetate. The organic phase is separated off, and washed twice with 100 ml of water and 100 ml of saturated sodium chloride solution. The organic phase is concentrated and forms a mixture of oil and crystals (22 g/yield 40%). After crystallization of the crude product from 160 ml of ethanol, 9.0 g of yellow crystals are obtained, m.p. 138–139°.

EXAMPLE 4

5-Bromobenzofuran-2-carboxylic Acid Dibenzylamide

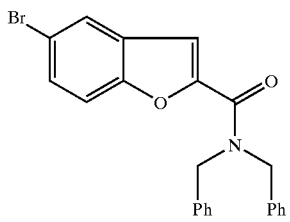

A solution of 50 ml of toluene and 7.9 g of dibenzylamine are added dropwise with stirring at 50–60° C. in the course of 10 min. to 5.2 g of 5-bromobenzofuran-2-carbonyl chloride in 100 ml of toluene. A colourless solid is obtained. After dropwise addition is complete, the mixture is additionally stirred at 100–110° C. for a further 3 hours. After cooling to 10° C., the solid product (dibenzylammonium chloride) is filtered off with suction. The filtrate is then treated with a mixture of 150 ml of water and 10 g of sodium carbonate and thoroughly shaken. The organic phase is separated off, washed again with 100 ml of water, dried using sodium sulfate and filtered. The, filtrate is concentrated on a Rotavapor in vacuo to a residue (residue: 9.5 g). After recrystallization from 100 ml of methanol, 6.5 g of product (yield 77%) remain after isolation.

m.p. 114–115°.

EXAMPLE 5

5-(4-Benzylpiperazin-1-yl)bromobenzofuran-2-carboxylic Acid Dibenzylamide

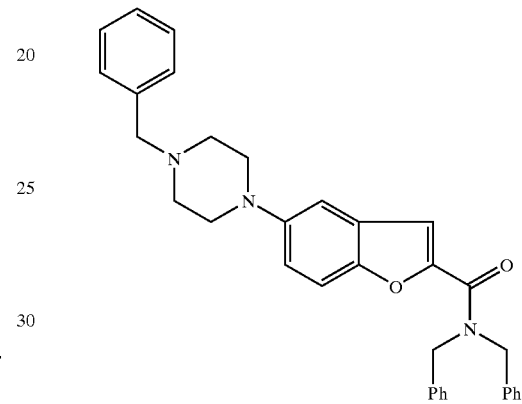

0.06 mg of Pd2DBA3 [sic] and 0.007 g of 2-dicyclohexylphosphino-2'-dimethylaminobiphenyl in 40 ml of toluene was stirred under nitrogen at 25° C. for 20 min. 1.58 g of 5-bromo-2,3-dihydrobenzofuran-2-carboxylic acid dibenzylamide, 0.98 g of 1-benzylpiperazine and 1.43 g of sodium tert-butylate are then added and the mixture is stirred at 120° C. for 2 hours. The cooled reaction mixture is stirred into a mixture of 150 ml of water and 5 ml of 37% hydrochloric acid with stirring [sic]. The reaction mixture is neutralized with 1.5 g of sodium carbonate and the phase is [sic] extracted 3 times with 100 ml of ethyl acetate. The combined organic phases are dried with 5 g of sodium sulfate and the filtrate is concentrated in vacuo to give a resinous residue (1.8 g of crude product). The crude product is dissolved in 100 ml of ethyl acetate, clarified with activated carbon and filtered. By addition of 25 ml of 2-molar ethanolic hydrochloric acid, the piperazine product is precipitated as the hydrochloride, filtered, and the crystals are washed with 10 ml of ethyl acetate and dried in vacuo at 40° C. Final weight: 1.5 g/yield 53%, m.p. 196–198°.

EXAMPLE 6 cis/trans-1,2-Di(5-Bromobenzofuran)-2-ylethene

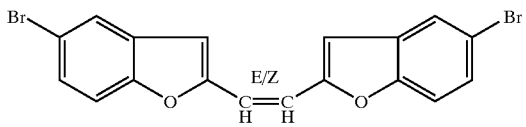

A) Preparation of the Diether

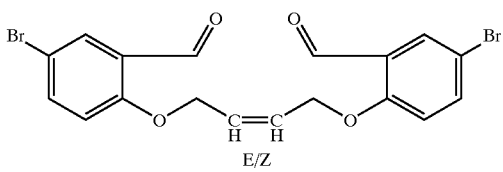

The compound is obtained by reaction of 5-bromosalicylaldehyde with Cl—CH$_2$—CH=CH—CH$_2$—Cl.

B) The Dibenzofuran Derivative is Obtained by Cyclization.

EXAMPLE 7

2,2'-Ethyndiyl-bis-5-bromobenzofuran

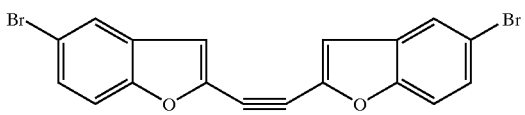

A) Preparation of the diether

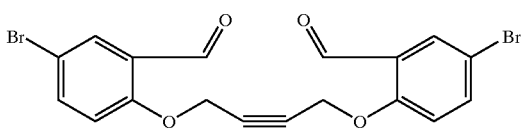

Reaction of 5-bromosalicylaldehyde with Cl—CH$_2$—CC—CH$_2$—Cl.

B) Cyclization of the Diether.

What is claimed is:

1. A benzofuran derivative of formula I

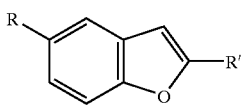

wherein
R is 1-piperazinyl, 4-R$^1$-piperazinyl or L,
R' is 2-R$^2$-5-R$^3$-pyrrol-1-ylcarbonyl, 4-R$^4$-piperazin-1-ylcarbonyl, N,N-di(tert-butyloxycarbonyl)aminocarbonyl, —CH=C(R$^5$R$^6$), benzofuran-2-yl-C≡C—, —C(Hal)$_3$, —CO—C(Hal)$_3$, 1,4-dihydrobenzo[d][1,2]oxazin-3-ylcarbonyl or 3,4-dihydrobenzo-1H-phthalazin-2-ylcarbonyl,
L is Cl, Br, I or an OH or a reactive functionally modified OH group,
R$^1$, R$^4$ in each case independently of one another are H, benzyl or another amino protective group,
R$^2$, R$^3$ in each independently of one another are H or alkyl having 1–6 C atoms,
R$^5$, R$^6$ in each case independently of one another are alkyl having 1–6 C atoms, and
Hal is F, Cl, Br or I,
or a salt thereof.

2. A compound selected from the group consisting of
a) (5-Bromobenzofuran-2-yl)-(2,5-dimethylpyrrol-yl)methanone
b) (4-Benzylpiperazin-1-yl)-[5-(4-benzylpiperazin-1-yl)benzofuran-2-yl]methanone;
c) [5-(4-Benzylpiperazin-1-yl)benzofuran-2-yl]-(1,4-dihydrobenzo[d][1,2]oxazin-3-ylmethanone;
d) [5-(4-Benzylpiperazin-1-yl)benzofuran-2-yl]-(3,4-dihydro-1H-phthalazin-2-yl)methanone; or
e) 5-Bromo-2-(2-methylpropenyl)benzofuran;
or a salt thereof.

3. A process for preparing a benzofuran derivative of formula I according to claim 1, wherein
R is Cl, Br, I, 1-piperazinyl or 4-R$^1$-piperazinyl, and
R' is 2-R$^2$-5-R$^3$-pyrrol-1-ylcarbonyl, 4-R$^4$-piperazin-1-ylcarbonyl, 1,4-dihydrobenzo[d][1,2]oxazin-3-ylcarbonyl or 3,4-dihydrobenzo-1H-phthalazin-2-ylcarbonyl,
said process comprising reacting a compound of formula II

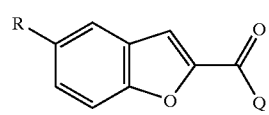

wherein
R is Cl, Br, I, 1-piperazinyl or 4-R$^1$-piperazinyl, and
Q is Cl, Br, I or an OH or a reactive functionally modified OH group,
wherein R$^1$ has the meaning indicated in claim 1,
with a compound of formula III

R'—H    III wherein
R' is 2-R$^2$-5-R$^3$-pyrrol-1-yl, 4-R$^4$-piperazin-1-yl, 1,4-dihydrobenzo[d][1,2]oxazin-3-yl or 3,4-dihydrobenzo-1H-phthalazin-2-yl,
wherein R$^2$, R$^3$ and R$^4$ have the meanings indicated in claim 1.

4. A method for preparing 1-[4-(5-cyanoindol-3-yl)butyl]-4-(2-carbamoylbenzofuran-5-yl)piperazine comprising reacting 3-R-6-hydroxybenzaldehyde, wherein R is Cl, Br or I, with a compound of formula VI

X—CH$_2$—CO—Q    VI wherein X is Cl, Br, I or an OH or a functionally modified OH group,
Q is OH or OR" and
R" is alkyl having 1–6 C atoms,
to provide a compound of formula VII

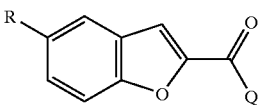

wherein
R is Cl, Br or I, and
Q has the meanings indicated above,
then converting Q into Cl, Br, I or a functionally modified OH group,
then reacting the resultant compound with a compound of formula III

R'—H    III wherein

R' is 2-R$^2$-5-R$^3$-pyrrol-1-ylcarbonyl, 4-R$^4$-piperazin-1-ylcarbonyl, 1,4-dihydrobenzo[d][1,2]oxazin-3-ylcarbonyl or 3,4-dihydrobenzo-1H-phthalazin-2-ylcarbonyl,
wherein
R$^4$ is H, benzyl or another amino protective group,
R$^2$, R$^3$ in each case independently of one another are H or alkyl having 1–6 C atoms,
to provide a compound of the formula I

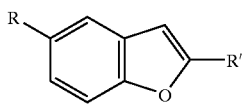

I wherein

R is Cl, Br or I,
R' is 2-R$^2$-5-R$^3$-pyrrol-1-ylcarbonyl, 4-R$^4$-piperazin-1-ylcarbonyl, 1,4-dihydrobenzo[d][1,2]oxazin-3-ylcarbonyl or 3,4-dihydrobenzo-1H-phthalazin-2-ylcarbonyl,
R$^4$ is H, benzyl or another amino protective group,
R$^2$, R$^3$ in each case independently of one another are H or alkyl having 1–6 C atoms,
then converting R of the resultant compound of formula I into another radical R, by reacting said compound of formula I under transition metal catalysis with a compound of formula VIII 4-R$^1$-piperazine      VIII wherein
R$^1$ is benzyl or an amino protective group, to provide a compound of the formula I
wherein
R is 4-R$^1$-piperazinyl,
R' is 2-R$^2$-5-R$^3$-pyrrol-1-ylcarbonyl, 4-R$^4$-piperazin-1-ylcarbonyl, 1,4-dihydrobenzo[d][1,2]oxazin-3-ylcarbonyl or 3,4-dihydrobenzo-1H-phthalazin-2-ylcarbonyl,
R$^1$ is benzyl or an amino protective group,
R$^4$ is H, benzyl or another amino protective group,
R$^2$, R$^3$ in each case independently of one another are H or alkyl having 1–6 C atoms,
followed by either
i) converting the resultant compound of formula I by basic hydrolysis into a compound of formula IX and/or its acid addition salt

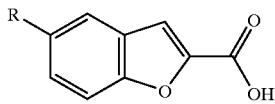

IX wherein
R is 4-R$^1$-piperazinyl and
R$^1$ is benzyl or another amino protective group,
and then converting the resultant compound of formula IX by using ammonia into a compound of formula X

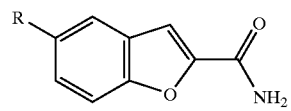

X wherein
R is 4-R$^1$-piperazinyl and
R$^1$ is benzyl or another amino protective group, or
ii) converting the resultant compound of formula I by using ammonia into a compound of formula X

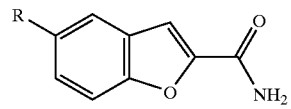

X wherein
R is 4-R$^1$-piperazinyl and
R$^1$ is benzyl or another amino protective group,
then converting the resultant compound of formula X into 5-(1-piperazinyl)benzofuran-2-carboxamide or an acid addition salt of it by removing the protective group R$^1$ and
reacting the 5-(1-piperazinyl)benzofuran-2-carboxamide with 3-(4-chlorobutyl)-5-cyanoindole to provide 1-[4-(5-cyanoindol-3-yl)butyl]-4-(2-carbamoylbenzofuran-5-yl)piperazine and optionally then converting it into its acid addition salt.

5. A process for preparing a benzofuran derivative of formula I according to claim 1 wherein
R is Cl, Br, I, 1-piperazinyl or 4-R$^1$-piperazinyl, and
R' is —CH=C(R$^5$R$^6$), benzofuran-2-yl-C≡C—, —C(Hal)$_3$ or —CO—C(Hal)$_3$,
wherein R$^1$, R$^5$ and R$^6$ have the meanings indicated in claim 1,
said process comprising reacting a compound of formula IV

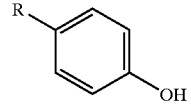

IV wherein R is Cl, Br, I, 1-piperazinyl or 4-R$^1$-piperazinyl, with a compound of formula V

Q'—CH$_2$—CO—R'      V wherein R' is —CH=C(R$^1$R$^6$), benzofuran-2-yl-C≡C—, —C(Hal)$_3$ or —CO—C(Hal)$_3$, and
Q' is Cl, Br, I or an OH or a reactive functionally modified OH group,
wherein R$^5$ and R$^6$ have the meanings indicated in claim 1.

6. A process for preparing a benzofuran derivative of formula I according to claim 1 wherein
R is Cl, Br, I, 1-piperazinyl or 4-R$^1$-piperazinyl, and
R' is —CH=C(R$^5$R$^6$), benzofuran-2-yl-C≡C—, —C(Hal)$_3$ or —CO—C(Hal)$_3$,
wherein R$^1$, R$^5$ and R$^6$ have the meanings indicated in claim 1,
said process comprising cyclizing a compound of formula Va

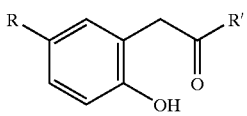

Va wherein

R is Cl, Br, I, 1-piperazinyl or 4-$R^1$-piperazinyl, and
R' is —CH=C($R^5R^6$), benzofuran-2-yl-C≡C—, —C(Hal)$_3$ or —CO—C(Hal)$_3$.

7. A process for preparing a benzofuran derivative of formula I according to claim 1 wherein R is a 1-piperazinyl radical, said process comprising converting by introducing an amino protective group into another compound of formula I wherein R is a 4-$R^1$-piperazinyl radical, and wherein $R^1$ is an amino protective group.

8. A process for preparing a benzofuran derivative of formula I according to claim 1 wherein R is a 4-$R^1$-piperazinyl group, and $R^1$ is benzyl or another amino protective group, said process comprising converting by removing the benzyl or another amino protective group into a compound of formula I wherein $R^1$ is 1-piperazinyl.

9. A process for preparing a benzofuran derivative of formula I according to claim 1 wherein in a compound of formula I a radical R is converted into another radical R, said process comprising replacing a Br atom by OH, esterifying an OH group or replacing a Br atom by a 4-$R^1$-piperazinyl group, wherein $R^1$ is benzyl or an amino protective group.

10. A process for preparing a salt of a benzofuran derivative of formula I according to claim 1 comprising converting a base of a compound of formula I into one of its salts by treatment with an acid.

11. A benzofuran derivative of formula I according to claim 1 wherein the reactive functionally modified OH group is selected from the group consisting of an activated ester, an imidazolide, an alkylsulfonyloxy having 1 to 6 Carbon atoms, and an arysulfonyloxy having 6 to 10 Carbon atoms.

12. A benzofuran derivative of formula I according to claim 1 wherein the reactive functionally modified OH group is selected from the group consisting of methylsulfonyloxy, phenyl-tolylsulfonyloxy and p-tolylsulfonyloxy.

13. A process according to claim 3, wherein Q is Cl or Br, and R is Br or 4-benzylpiperazinyl.

14. A process according to claim 5, wherein Q' is Cl or Br, and R is Br or 4-benzylpiperazinyl.

15. A method of preparing a pharmaceutical compound wherein a compound of formula I according to claim 1 is an intermediate compound in the synthesis of the pharmaceutical compound.

16. A method of treating a condition of the central nervous system comprising administering an effective amount of a compound prepared by a method according to claim 15 to a patient.

* * * * *

UNITED STATES PATENT AND TRADEMARK OFFICE
CERTIFICATE OF CORRECTION

PATENT NO. : 6,531,503 B1
APPLICATION NO. : 10/030471
DATED : March 11, 2003
INVENTOR(S) : Andreas Bathe et al.

It is certified that error appears in the above-identified patent and that said Letters Patent is hereby corrected as shown below:

On Title Page, (75) second inventor's address reads "Obert-Ramstadt" should read -- Ober-Ramstadt --
Column 13, line 7, reads "$R^{2, R3}$" should read -- $R^2, R^3$ --
Column 14, line 54, reads $(R^1R^6)$ should read -- $(R^5R^6)$ --

Signed and Sealed this

Twenty-second Day of August, 2006

JON W. DUDAS
*Director of the United States Patent and Trademark Office*